US006077542A

United States Patent [19]

Sherman

[11] Patent Number: 6,077,542
[45] Date of Patent: Jun. 20, 2000

[54] SOLID SUBSTANCES COMPRISING VALPROIC ACID AND SODIUM VALPROATE

[76] Inventor: Bernard Charles Sherman, 50 Old Colony Road, Willowdale, Canada, M2L 2K1

[21] Appl. No.: 08/875,597

[22] PCT Filed: Jan. 19, 1996

[86] PCT No.: PCT/CA96/00040

§ 371 Date: Jul. 31, 1997

§ 102(e) Date: Jul. 31, 1997

[87] PCT Pub. No.: WO96/23491

PCT Pub. Date: Aug. 8, 1996

[30] Foreign Application Priority Data

Feb. 2, 1995 [NZ] New Zealand .............................. 270438

[51] Int. Cl.[7] ....................................................... A61K 9/16

[52] U.S. Cl. ........................... 424/489; 424/495; 514/557; 562/606

[58] Field of Search ..................................... 424/489, 495; 514/557; 562/606

[56] References Cited

U.S. PATENT DOCUMENTS

| 4,675,236 | 6/1987 | Ohkawara | 428/402 |
| 5,017,613 | 5/1991 | Aubert | 514/557 |
| 5,212,326 | 5/1993 | Meade | 562/606 |

*Primary Examiner*—Donald E. Adams
*Assistant Examiner*—D. Faulkner
*Attorney, Agent, or Firm*—Nixon & Vanderhye P.C.

[57] ABSTRACT

Substances that are solid at 25° C. are obtained by dissolving sodium valproate in heated valproic acid and cooling the resultant solution. The resulting solid substances can easily be processed into solid pharmaceutical dosage forms.

8 Claims, No Drawings

SOLID SUBSTANCES COMPRISING VALPROIC ACID AND SODIUM VALPROATE

This application is a 371 of PCT CA 96/00040 filed Jan. 19, 1996.

BACKGROUND OF THE INVENTION

Valproic acid and sodium valproate are drugs useful for the treatment of epileptic seizures or convulsions.

Valproic acid has molecular formula $C_8H_{16}O_2$ and molecular weight 144.21. It is a liquid at room temperature (20° C. to 30° C.) and thus is not suitable for manufacture of solid pharmaceutical dosage forms such as tablets for oral administration.

Sodium valproate is the sodium salt of valproic acid. It has molecular formula $C_8H_{15}O_2N_a$ and molecular weight 166.19. It is a solid at room temperature and does not melt even at substantially higher temperatures. It is thus more suitable than valproic acid for manufacture of solid dosage forms. However, sodium valproate is highly hygroscopic and readily absorbs water from the atmosphere, which leads to problems of poor stability of compositions made from sodium valproate.

It is thus desirable to have a material that combines certain properties of sodium valproate with certain properties of valproic acid. That is to say, it is desirable to have a substance with the therapeutic properties of valproic acid or sodium valproate which, like sodium valproate, is a solid at room temperature but, like valproic acid, is non-hygroscopic.

U.S. Pat. No. 5,212,326 describe such a substance. It is described as being an oligomer having at 1:1 molar ratio of sodium valproate and valproic acid. That substance is now known by the name divalproex sodium.

According to U.S. Pat. No. 5,212,326, divalproex sodium is made by dissolving one mole each of valproic acid and sodium valproate in acetone and cooling the solution to 0° C. to precipitate the compound. Alternately, it is made by adding one mole of sodium hydroxide dissolved in an acetone-miscible solvent to two moles of valproic acid dissolved in acetone and evaporating the solvents.

As described in U.S. Pat. No. 5,212,326, this new compound, divalproex sodium, represents a new single chemical molecule.

Divalproex sodium has molecular formula $C_{16}H_{31}O_4N_a$ and molecular weight 310.4. The molecular formula is the sum of the molecular formulas of valproic acid and sodium valproate, and similarly the molecular weight is the sum of the two molecular weights. It has a melting point of about 100° C.

While divalproex sodium as disclosed in U.S. Pat. No. 5,212,326 has the desired features of being a nonhygroscopic solid, it has the disadvantage of requiring the use of acetone or other organic solvents to prepare it from valproic acid and sodium valproate or sodium hydroxide.

The organic solvents are expensive and also give rise to concerns about toxic effects on production personnel and environmental concerns relating to disposal of the solvent.

It is thus the object of the present invention to enable production of a substance that is functionally equivalent to divalproex sodium as disclosed in U.S. Pat. No. 5212316, in that it is a nonhygroscopic solid, but that can be made from valproic acid and sodium valproate without use of organic solvents.

SUMMARY OF THE INVENTION

Sodium valproate is somewhat soluble in valproic acid. At room temperature (about 25° C.) the amount of sodium valproate that can be dissolved in valproic acid is about 50 g sodium valproate per 100 g valproic acid. At this temperature, further quantity of sodium valproate will not dissolve, regardless of blending time. In other words, the saturation point is about 50 g sodium valproate per 100 g valproic acid at about 25° C.

As the amount of sodium valproate dissolved in valproic acid is increased, the melting point (or freezing point) of the solution also increases. At a concentration of 50 g sodium valproate per 100 g valproic acid, the melting point is still below room temperature, so that a saturated solution consisting of about 50 g sodium valproate per 100 g valproic acid is still a liquid at room temperature.

It has been found that, as temperature is increased above room temperature, the amount of sodium valproate that can be dissolved in valproic acid increases. The melting point of the solution also increases as the ratio of sodium valproate to valproic acid is increased.

The essence of the invention is to heat valproic acid to a temperature substantially above room temperature, to dissolve sodium valproate in the hot valproic acid, the quantity of sodium valproate being substantially above 50 g sodium valproate per 100 g valproic acid, so as to form a solution that has a melting point/freezing point above room temperature and to cool the solution to room temperature, whereupon it solidifies. The result is a substance which is solid at room temperature and is comprised of valproic acid and sodium valproate, the amount of sodium valproate therein being in excess of 50 g sodium valproate per 100 g valproic acid.

The solid substance can then be ground up into solid granules for further processing into solid dosage forms such as tablets.

It will be understood that substances made according to this invention may optionally comprise other ingredients in addition to valproic acid and sodium valproate. That is to say, other ingredients may be incorporated into the hot liquid blend of valproic acid and sodium valproate before it is solidified, and/or other ingredients may be added after the liquid is solidified and ground into granules, by mixing such other ingredients with the granules.

DETAILED DESCRIPTION OF THE INVENTION

As aforesaid, by heating valproic acid to a temperature above room temperature, the amount of sodium valproate that can be dissolved therein is increased, and the melting point also increases. If sufficient sodium valproate is thereby added such as to increase the melting point to above room temperature, the solution becomes a solid upon cooling to room temperature.

Also as aforesaid, only about 50 g sodium valproate can be dissolved in 100 g valproic acid at room temperature, so that in excess of 50 g sodium valproate per 100 g valproic acid must be used to give a solid at room temperature.

In one experiment, sodium valproate was dissolved in heated valproic acid in a ratio of 80 g, sodium valproate per 100 g valproic acid. The solution solidified upon cooling to room temperature. Upon reheating the substance was found to begin to melt at a temperature of about 73° C.

While a melting point of 73° C. is sufficiently above room temperature to enable the solution to be ground into granules and further processed into solid dosage forms such as tablets, it is preferable to have a substance with an even higher melting point, most preferably above 90° C. This is because heat is generated in the process of grinding the solid substance into granules; with a melting point of only about 73° C., the substance may tend to become soft in the grinding process, making it difficult to complete the grinding.

The melting point of the solid substance can be increased to above 73° C. by further increasing the ratio of sodium valproate to valproic acid.

In a further experiment, sodium valproate was dissolved in valproic acid in a ratio of 100 g sodium valproate to 100 g valproic acid. The blending was done at a temperature of about 165° C. The solution was cooled to room temperature, again resulting in a solid substance. Upon the reheating, it was found that the melting point was about 100° C.

From the foregoing it might be expected that by further increasing the ratio of sodium valproate to valproic acid, the melting point of the substance can be further increased. Surprisingly, this is not the case. In further experiments, the ratio of sodium valproate to valproic acid was increased to as much as 160 g sodium valproate per 100 g valproic acid, with blending at temperature up to 220° C. In each case, a solid substance was again formed upon cooling to room temperature. On reheating of these solids, in each case it was found that the solid began to melt at a temperature of about 100° C.

The reason for this phenomenon appears to be that when the ratio of sodium valproate to valproic acid reaches 100 g per 100 g, which gives a melting point of about 100° C., the solution is a saturated solution at the melting point. If an additional amount of sodium valproate is added, it thus is not dissolved in the hot liquid at about 100° C, but is present as undissolved sodium valproate.

Even if an additional amount of sodium valproate is added (i.e. above 100 g per 100 g valproic acid) and it is fully dissolved by blending at well above 100° C., as the solution is cooled down to about 100° C., some of the sodium valproate precipitates. As solidification occurs, what results is a solid saturated solution of sodium valproate in valproic acid plus extra precipitated sodium valproate.

It thus follows that so long as the ratio of sodium valproate to valproic acid is above about 100 g per 100 g, the solid substance will begin to melt at a temperature of about 100° C. regardless of the ratio.

Nevertheless, a melting point of about 100° C. is more than sufficient to provide a substance that fully meets the object of the invention. That is to say, it is a solid at room temperature, is easily workable for further processing, and is relatively nonhygroscopic. The substances of this invention are thus functionally equivalent to the divalproex sodium produced according to U.S. Pat. No. 5,212,326.

The operation of the invention will be further understood from the following examples, which are intended to be illustrative and not limiting of the invention.

EXAMPLE 1

Sodium valproate was added to valproic acid in a ratio of 100 g sodium valproate to 100 g valproic acid and the mixture was blended at a temperature above 100° C. until the sodium valproate was fully dissolved. The solution was cooled to room temperature and the resultant solid was ground into granules. When the granules were reheated, the melting range was found to be about 100° C.

EXAMPLE 2

Sodium valproate was added to valproic acid in a ratio of 115.2 g sodium valproate to 100 g valproic acid and the mixture was blended at about 150° C. until the sodium valproate was fully dissolved to give a clear solution. The solution was cooled to room temperature and the resultant solid was ground into granules. When the granules were reheated, the melting range was found to be about 100° C. As the ratio of 115.2 g sodium valproate to 100 g valproic acid is 1 mole per mole, the substance of this experiment has the same composition as the divalproex sodium of U.S. Pat. No. 5,212,326.

EXAMPLE 3

As in example 2, sodium valproate was added to vaproic acid in a ratio of 115.2 g sodium valproate to 100 g valproic acid. However, the blending was done at a temperature of only 100° C. It could be seen that not all of the sodium valproate became dissolved, as particles of undissolved sodium valproate remained visible. The mixture was cooled to room temperature and the resultant solid was ground into granules. When the granules were reheated, they melted at about 100° C. but solid particles, apparently being the undissolved portion of the sodium valproate, were visible in the melt.

The solid substance made by this example is again functionally equivalent to the divalproex sodium of U.S. Pat. No. 5,212,326, but it is not the same at the molecular level, as it is not an oligomer, but is a mixture of a solution of sodium valproate in valproic acid plus undissolved sodium valproate.

EXAMPLE 4

Granules for example 1 were mixed with additional sodium valproate in the following ratio:

| | |
|---|---|
| granules of example 1 | 200.0 |
| sodium valproate | 15.2 |
| Total | 215.2 | the ratio of sodium valproate to valproic acid in this mixture is the same as in Example 2 and Example 3, so that this mixture again has the same composition as the divalproex sodium of U.S. Pat. No. 5,212,326.

EXAMPLE 5

Sodium valproate was added to valproic acid in a ratio of 120 g sodium valproate to 100 parts valproic acid and the mixture was blended at about 185° C. The solution was cooled to room temperature and the resultant solid ground into granules. When the granules were reheated, the melting range was found to be about 100° C.

EXAMPLE 6

Granules from example 1 were mixed with granules of example 5 in the following ratio:

granules of example 1—1 part
granules of example 5—3.17 parts

The ratio of sodium valproate to valproic acid in this mixture is again the same as in Example 2, 3 and 4, so that this mixture again has the same composition as the divalproex sodium of U.S. Pat. No. 5,212,326.

EXAMPLE 7

Ingredients were mixed in the following ratio:

| | |
|---|---|
| granules from example 2 | 540. |
| microcrystalline cellulose | 400. |
| magnesium stearate | 18. |
| colloidal silicon dioxide | 2. |
| Total: | 960. |

This mixture was compressed into tablets with a weight of 960 mg per tablet, so that each tablet contained the equivalent of 540 mg of divalproex sodium, which is equivalent to 500 mg of valproic acid.

EXAMPLE 8

Ingredients were mixed in the following ratio:

| | |
|---|---|
| granules from example 3 | 540. |
| microcrystalline cellulose | 400. |
| magnesium stearate | 18. |
| colloidal silicon dioxide | 2. |
| Total: | 960. |

This mixture was compressed into tablets with a weight of 960 mg per tablet, so that each tablet contained the equivalent of 540 mg of divalproex sodium, which is equivalent to 500 mg of valproic acid.

EXAMPLE 9

Ingredients were mixed in the following ratio:

| | |
|---|---|
| mixture from example 4 | 540. |
| microcrystalline cellulose | 400. |
| magnesium stearate | 18. |
| colloidal silicon dioxide | 2. |
| Total: | 960. |

This mixture was compressed into tablets with a weight of 960 mg per tablet, so that each tablet contained the equivalent of 540 mg of divalproex sodium, which is equivalent to 500 mg of valproic acid.

EXAMPLE 10

Ingredients were mixed in the following ratio:

| | |
|---|---|
| mixture from example 6 | 540. |
| microcrystalline cellulose | 400. |
| magnesium stearate | 18. |
| colloidal silicon dioxide | 2. |
| Total: | 960. |

This mixture was compressed into tablets with a weight of 960 mg per tablet, so that each tablet contained the equivalent of 540 mg of divalproex sodium, which is equivalent to 500 mg of valproic acid.

What is claimed is:

1. A process of making a solid substance comprising valproic acid and sodium valproate which process comprises the steps of heating the valproic acid, dissolving sodium valproate therein, and cooling the resultant solution to below the melting point.

2. A process as in claim 1 wherein the quantity of sodium valproate by weight exceeds fifty percent of the quantity of valproic acid by weight and the sodium valproate is blended with the valproic acid at a temperature above 30° C.

3. A process as in claim 2 wherein the quantity of sodium valproate by weight exceeds 80 percent of the quantity of valproic acid by weight and the sodium valproate is blended with the valproic acid at a temperature above 40° C.

4. A process as in claim 3 wherein the quantity of sodium valproate valproate exceeds 90 percent of the quantity of valproic acid by weight and the sodium valproate is blended with the valproic acid at a temperature above 90° C.

5. A homogenous substance that is a solid at room temperature and is made according to the process of claim 1.

6. A solid pharmaceutical composition which comprises said solid substance according to claim 5, wherein said solid substance is in granular form, and optionally comprises other ingredients.

7. A solid pharmaceutical composition according to claim 6 which also comprises additional sodium valproate that has not been dissolved in valproic acid.

8. A solid pharmaceutical composition which comprises two different types of solid substances according to claim 5, wherein the two different types of solid substances are in granular form and differ from each other in having different ratios of sodium valproate to valproic acid, said composition optionally also comprising other ingredients.

\* \* \* \* \*